(12) United States Patent
Lorenzo

(10) Patent No.: US 9,980,731 B2
(45) Date of Patent: May 29, 2018

(54) EMBOLIC COIL DETACHMENT MECHANISM WITH FLEXIBLE DISTAL MEMBER AND COUPLING UNION

(75) Inventor: Juan A. Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1296 days.

(21) Appl. No.: 13/436,638

(22) Filed: Mar. 30, 2012

(65) Prior Publication Data
US 2013/0261659 A1 Oct. 3, 2013

(51) Int. Cl.
A61M 29/00 (2006.01)
A61B 17/12 (2006.01)
A61B 17/00 (2006.01)

(52) U.S. Cl.
CPC .. *A61B 17/12031* (2013.01); *A61B 17/12113* (2013.01); *A61B 17/12154* (2013.01); *A61B 2017/00004* (2013.01); *A61B 2017/00871* (2013.01); *A61B 2017/12068* (2013.01); *A61B 2017/12072* (2013.01); *A61B 2017/12077* (2013.01)

(58) Field of Classification Search
CPC ........ A61B 17/12022; A61B 17/12031; A61B 17/12113; A61B 17/12154; A61B 2017/00871; A61B 2017/12072; A61B 2017/12077; A61B 2017/12068; A61B 2017/00004
USPC .................................................. 606/200, 191
See application file for complete search history.

(56) References Cited

U.S. PATENT DOCUMENTS

| | | | |
|---|---|---|---|
| 5,578,074 A | 11/1996 | Mirigian | |
| 5,911,737 A | 6/1999 | Lee et al. | |
| 5,989,242 A | 11/1999 | Saadat et al. | |
| 6,059,815 A | 5/2000 | Lee et al. | |
| 6,102,917 A * | 8/2000 | Maitland et al. | 606/108 |
| 6,102,933 A | 8/2000 | Lee et al. | |

(Continued)

FOREIGN PATENT DOCUMENTS

| | | |
|---|---|---|
| CN | 101310681 A | 11/2009 |
| CN | 101668490 A | 3/2010 |

(Continued)

OTHER PUBLICATIONS

EPO, Partial European Search Report from European Patent Application No. EP 13162030 dated Jul. 20, 2013.

*Primary Examiner* — Son Dang

(57) ABSTRACT

Provided herein are a system and method for detaching a therapeutic device, e.g. an embolic coil, from a delivery tube at a target site in a patient's body. The system includes a bead disposed against a distal end of the therapeutic device that retains the therapeutic device to the delivery tube in a first compressed configuration through a coupling union comprising a series of connectors. The series of connectors may include a stretch resistant member through which the bead is attached to an anchor inside the therapeutic device. The anchor, in turn, may be disposed against a thermally responsive element comprised of a polymeric material configured to melt or otherwise change configuration to release the anchor, and with it, to also release the therapeutic device. Energy may be supplied to the thermally responsive element through electrical conductors and a resistive heating element disposed within the delivery tube.

13 Claims, 2 Drawing Sheets

(56) References Cited

U.S. PATENT DOCUMENTS

| | | |
|---|---|---|
| 6,743,236 B2 | 6/2004 | Barry et al. |
| 7,578,826 B2 | 8/2009 | Gandhi et al. |
| 7,582,101 B2 | 9/2009 | Jones et al. |
| 7,591,833 B2 | 9/2009 | Jones et al. |
| 7,744,604 B2 | 6/2010 | Maitland et al. |
| 7,776,054 B2 | 8/2010 | Gandhi et al. |
| 7,780,680 B2 | 8/2010 | Gandhi et al. |
| 7,972,342 B2 | 7/2011 | Gandhi et al. |
| 8,192,480 B2* | 6/2012 | Tieu ............ A61F 2/95 623/1.11 |
| 8,328,860 B2* | 12/2012 | Strauss ........ A61B 17/12022 623/1.11 |
| 8,535,345 B2* | 9/2013 | Desai ........... A61B 17/12022 606/200 |
| 2003/0120300 A1* | 6/2003 | Porter ............................ 606/191 |
| 2004/0002732 A1* | 1/2004 | Teoh ............ A61B 17/12022 606/200 |
| 2005/0149108 A1* | 7/2005 | Cox .............................. 606/200 |
| 2006/0025801 A1 | 2/2006 | Lulo et al. |
| 2009/0062726 A1* | 3/2009 | Ford et al. ...................... 604/57 |
| 2009/0177261 A1* | 7/2009 | Teoh et al. ................... 623/1.11 |
| 2010/0094395 A1 | 4/2010 | Kellett |
| 2010/0137898 A1 | 6/2010 | Teoh |
| 2010/0160944 A1* | 6/2010 | Teoh ............ A61B 17/12022 606/191 |
| 2010/0249823 A1 | 9/2010 | Gandhi |
| 2010/0305606 A1 | 12/2010 | Gandhi |
| 2012/0022581 A1 | 1/2012 | Wilson |

FOREIGN PATENT DOCUMENTS

| | | |
|---|---|---|
| EP | 1738693 A | 1/2007 |
| JP | 07-037203 U | 7/1995 |
| JP | 2005530592 A | 10/2005 |
| JP | 2007007418 A | 1/2007 |
| JP | 2011147808 A | 8/2011 |
| WO | 2007109621 A2 | 9/2007 |
| WO | 2008112435 A2 | 9/2008 |

* cited by examiner

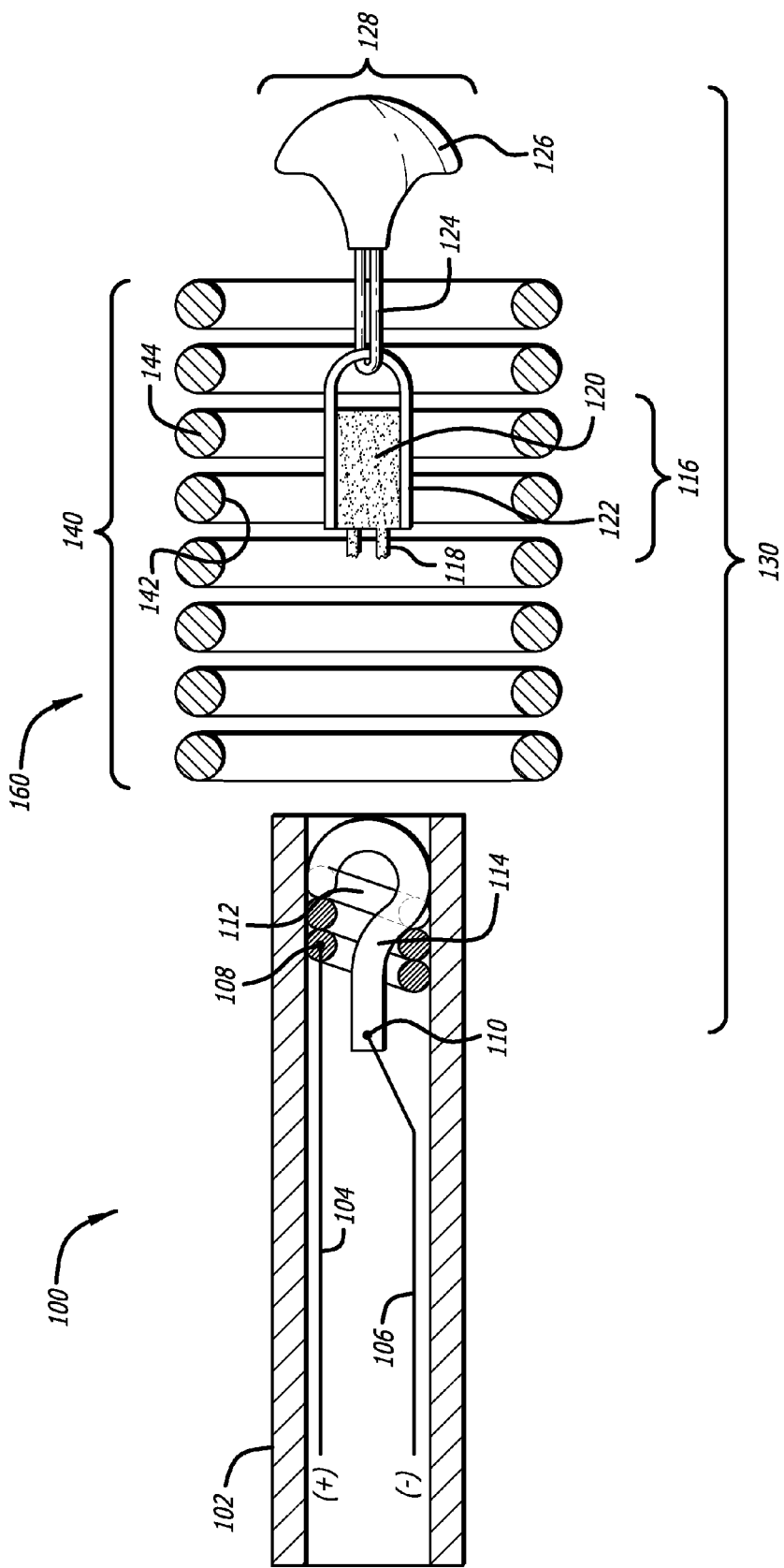

EMBOLIC COIL DETACHMENT MECHANISM WITH FLEXIBLE DISTAL MEMBER AND COUPLING UNION

BACKGROUND

The present invention relates to a medical device for placing an embolic coil at a preselected location within a vessel of the human body, and more particularly, relates to a flexible delivery member having a heating element and a heat responsive coupling member at the distal tip of the delivery member for holding the embolic coil in order to transport the coil to a desired position within the vessel and release the embolic coil at that position.

For many years flexible catheters have been used to place various devices within the vessels of the human body. Such devices include dilatation balloons, radiopaque fluids, liquid medications and various types of occlusion devices such as balloons and embolic coils. Occlusion devices including embolic coils can be used to treat aneurysms or to occlude a blood vessel at a target location.

Coils which are placed in vessels may take the form of helically wound coils, or alternatively, may be randomly wound coils, convoluted coils, coils wound within other coils or many other such configurations to better occlude a blood vessel. Embolic coils are generally formed of radiopaque biocompatible metallic materials, such as platinum, gold, tungsten, or alloys of these metals. The coils can be coated with various materials to improve thrombogenicity. Often times, several coils are placed at a given location in order to occlude the flow of blood through the vessel by promoting thrombus formation at the particular location. The decreased blood flow reduces the pressure on the aneurysm and reduces the risk of a ruptured aneurysm.

In the past, embolic coils have been placed within the distal end of the catheter. When the distal end of the catheter is properly positioned the coil may then be pushed out of the end of the catheter with, for example, a guidewire to release the coil at the desired location. This procedure of placement of the embolic coil is conducted under fluoroscopic visualization such that the movement of the coil through the vasculature of the body may be monitored and the coil may be placed at the desired location. With these placements systems there is very little control over the exact placement of the coil since the coil may be ejected to a position some distance beyond the end of the catheter.

Patients with potentially life-threatening hemorrhagic brain aneurysms are in need of a safe, reliable, and fast release mechanism for the deposition of embolic coils via catheters. Numerous procedures have been developed to enable more accurate positioning of coils within a vessel. One commercial product of current use is the Guglielmi Detachable Coil (GDC). The GDC utilizes the electrolytical dissolution of a designated guidewire junction to generate the release action. This procedure typically takes 10-30 minutes and is difficult to control in a reliable fashion. The effects of the dissolved material in the blood stream create a potential hazard to the patient. Problems that have been associated with the release of the coil include the force of the coil exiting the delivery catheter causing the coil to overshoot the desired site or dislodge previously deployed coils. Thus, even with the numerous prior efforts to develop miniature actuators for catheter-based therapeutic application, there remains a need for safe, fast release actuator mechanisms for the delivery of embolic coils, for example.

Another problem with embolic coil delivery systems that rely on a stiff pusher wire extending through the entire length of the catheter to push an element out of the distal end of the catheter is that the pusher wire inherently causes the catheter to be very stiff with the result that it is very difficult to guide the catheter through the vasculature of the body. Accordingly, there is a need for a mechanism for deploying embolic coils from the distal end of a catheter having a flexible body.

There is also a need for precise therapeutic actuators configured to deploy therapeutic elements or devices, e.g. embolic coils, within the narrow confines of blood vessels in the human brain, e.g. 250-500 micrometers in diameter. The present invention satisfies these and other needs.

SUMMARY OF THE INVENTION

Briefly and in general terms, the present invention provides for a release mechanism, a therapeutic actuator, or a system for delivering a therapeutic element or device to a target location. The target location may be a site within the vasculature of the human body, for example, a blood vessel in the brain in order to treat an aneurysm.

In its most basic form, the release mechanism includes a therapeutic element, such as an embolic coil, secured to a heating and delivery system through a polymer filament. Upon sufficient heat transfer from the heating and delivery system to the polymer filament the connection between the heating and delivery system and the therapeutic element is severed. This severance may occur through melting of the polymer which may cause it to break into two separate parts and to disengage from the connector element securing it to the heating and delivery system, thereby decoupling the coupling union. Or, severance of the connection between the therapeutic element and the heating and delivery system through the polymer filament may occur by the filament undergoing a phase transformation which causes it to deform in a manner that releases it from engagement with the connector element securing it to the heating and delivery system. For example, if one end of the polymer filament is enlarged to retain itself in position through a hole in the connector element, heating the polymer filament may cause the enlarged region to narrow and slide through the hole in the connector element, thereby releasing the therapeutic element from the heating and delivery system.

In a first of several aspects, the present invention accordingly provides for a therapeutic actuator for delivering a therapeutic element or device to a target location, such as a site within the vasculature of a human body. In a presently preferred aspect, the therapeutic element is an embolic coil configured for treatment of an aneurysm. The therapeutic actuator includes a polymeric element having a filament portion that secures a therapeutic element to a heating and delivery system. In a presently preferred aspect, the polymeric element includes an aggregate portion disposed within an internal lumen defined by the therapeutic element. The heating and delivery system preferably includes an electrical conductor disposed within the lumen of the flexible tube and a resistive heating element also disposed within the lumen of the flexible tube distal to the electrical conductor and electrically connected to the electrical conductor, and the filament portion is connected to the resistive heating element and the aggregate portion positioned inside the therapeutic element and distal to the filament portion. In another presently preferred aspect, the electrical conductor includes a positively charged electrical conductor and a negatively charged electrical conductor.

A bead on a distal end of the therapeutic element retains the therapeutic element in a compressed configuration through a coupling union including the filament portion that secures the bead to the heating and delivery system. In a presently preferred aspect, a distal face of the bead can have a hemispherical shape, or a curved outer surface that facilitates atraumatic introduction of the therapeutic element, for example.

In one presently preferred aspect, the therapeutic actuator also includes a flexible tube defining a lumen therein, wherein the therapeutic element is configured to be retained to the flexible tube, and the coupling union includes at least one additional connector securing the distal bead to the heating and delivery system. In a presently preferred aspect, the at least one additional connector of the coupling union that secures the distal bead to the heating and delivery system to maintain the therapeutic element in a compressed configuration includes an anchor disposed around the aggregate portion of the polymeric element between an outer surface of the aggregate portion and an inner surface of the therapeutic element.

In another presently preferred aspect, the anchor has a horseshoe shape. In another presently preferred aspect, the at least one additional connector of the coupling union that secures the distal bead to the heating and delivery system to maintain the therapeutic element in a compressed configuration further includes a stretch resistant member that secures the bead to the anchor. In another presently preferred aspect, the at least one additional connector of the coupling union that secures the distal bead to the heating and delivery system to maintain the therapeutic element in a compressed configuration includes a thermally conductive hook disposed between the filament portion and the resistive heating element, the hook connecting the filament portion of the polymeric element to the resistive heating element.

In another presently preferred aspect, the therapeutic actuator is configured such that the filament portion is disconnectable from the resistive heating element to release and deploy the therapeutic element from a distal end of the flexible tube by melting the polymeric element through energy supplied by the electrical conductor that heats the resistive heating element. In another presently preferred aspect, the polymeric element is formed of a shape memory material that undergoes a phase transformation at a phase transformation temperature whereby heating the material above the phase transformation temperature enables the material to soften and be reshaped to another configuration in which the filament portion disconnects from the resistive heating element and releases the therapeutic element for deployment from a distal end of the flexible tube.

In another presently preferred aspect, the present invention provides for a release mechanism for delivering a therapeutic element or device to a target location, such as a site within the vasculature of a human body, such as a blood vessel in the brain in order to treat an aneurysm, for example. The release mechanism includes a delivery member, an object to be released from the delivery member, and a bead connected to the object and the delivery member, at least in part through a polymeric element configured to undergo a transformation upon heating to thereby release the object from the delivery member.

In another presently preferred aspect, the present invention provides for a system for delivery of a therapeutic device to a target location, such as a site within the vasculature of a human body, such as a blood vessel in the brain in order to treat an aneurysm, for example. The system preferably includes an energy source, a thermally responsive element connected to the energy source, a polymeric element connected to the thermally responsive element, and an anchor that retains a therapeutic device to the polymeric element. In a presently preferred aspect, the polymeric element is formed of a material that changes configuration upon heating above a first temperature from heat supplied through the thermally responsive element, thereby releasing the anchor retaining the therapeutic device. In another presently preferred aspect, the anchor is formed of a material that maintains a fixed configuration upon heating to the first temperature. In another presently preferred aspect, the anchor is metallic. In another presently preferred aspect, the energy source may be one or more of an electrical conductor, a laser, an optical fiber, a solar cell, or a pressurized fluid, for example.

In another presently preferred aspect, the present invention provides for a method for deploying a therapeutic device to a target location, such as a site within the vasculature of a human body, such as a blood vessel in the brain in order to treat an aneurysm, for example. The method includes the steps of delivering a flexible tube connected to and retaining a therapeutic device to a target location in a body, supplying energy to heat a thermally responsive element that retains the therapeutic device to the flexible tube, melting the thermally responsive element, and releasing the therapeutic device to deploy the therapeutic device at the target location.

These and other features of the present invention will become apparent from the following detailed description of the preferred embodiments in conjunction with the accompanying drawings, which illustrate, by way of example, the operation of the invention.

BRIEF DESCRIPTION OF THE DRAWINGS

FIG. 1B is a side view of a system for delivery of a therapeutic device in accordance with an embodiment of the present invention with the therapeutic device in a second deployed configuration.

DETAILED DESCRIPTION OF THE PREFERRED EMBODIMENTS

Figure 1A:
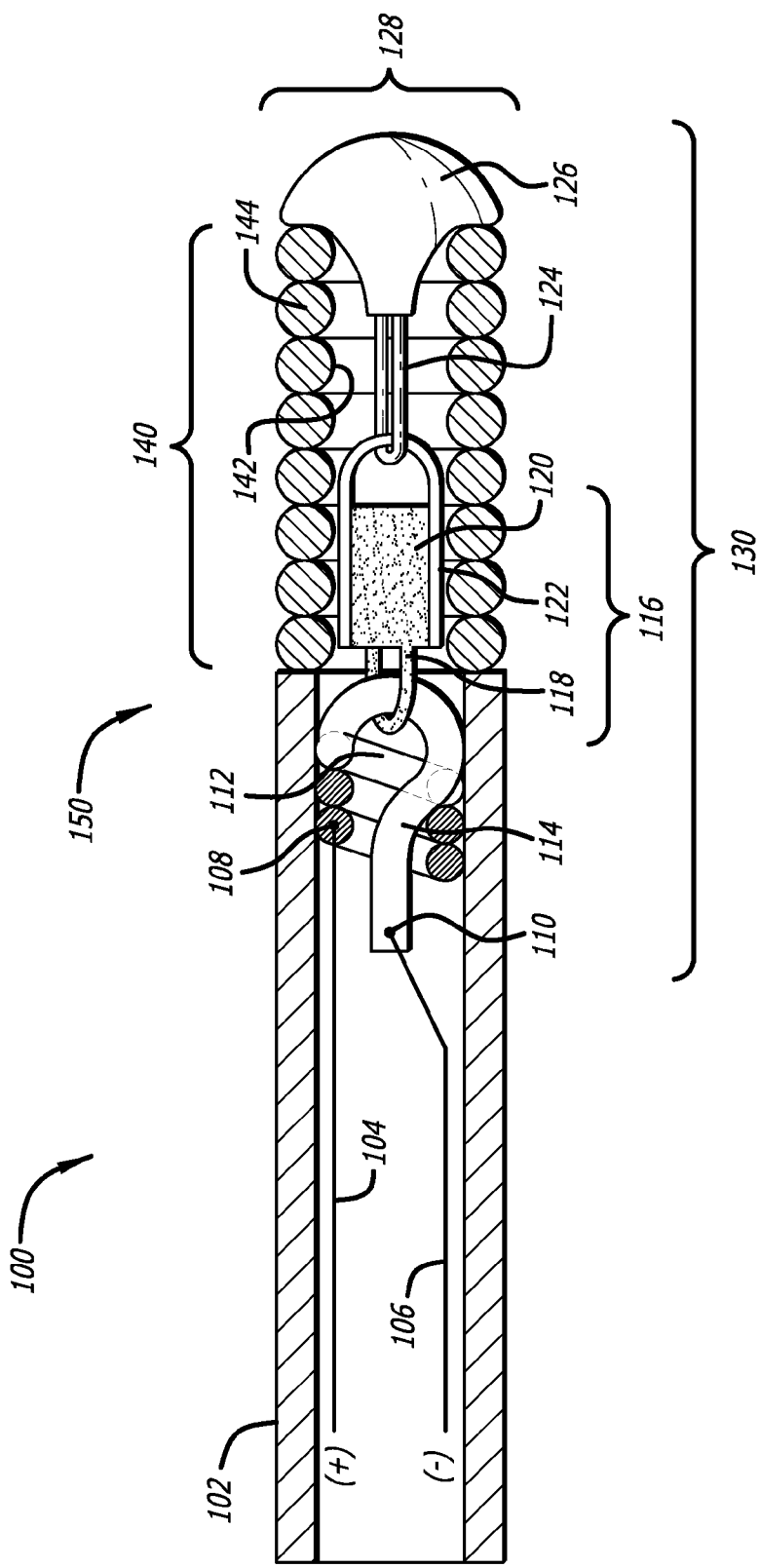
FIG. 1A is a side view of a system for delivery of a therapeutic device in accordance with an embodiment of the present invention with the therapeutic device in a first retained configuration.

Referring to the drawings, which are provided by way of example, and not by way of limitation, the present invention provides for a therapeutic element delivery system 100 (which may also be referred to as a therapeutic actuator or a release mechanism) including a flexible tube 102 for delivering a therapeutic element 140 to a target site within a body and a coupling union 130, that may be thermally decoupled, securing the therapeutic element 140 to the flexible tube 102. The therapeutic element 140 may be an embolic coil 144 or another occlusive device that serves to occlude an aneurysm by filling the aneurysm pouch, creating a physical barrier to reduce blood flow into the aneurysm, and inducing thrombosis or clotting therein. Examples of other types of vaso-occlusive devices known in the art that the therapeutic element may be or may incorporate include hydrogels, foams, bioactive coils, braids, cables and hybrid devices having a suitable configuration for attachment to the heating and delivery system. In some embodiments, the therapeutic element may be filled with a fibrous or other material or coated with a biogel or other substance that serves to promote clotting.

The delivery tube 102 that retains the therapeutic element 140 during introduction may be flexible along its entire length or the flexible region may be restricted to the distal end of the tube. The therapeutic element 140 is secured to the flexible tube 102 through a coupling union 130. The coupling union 130 may include any combination or sub-combination of a hook 114, a polymer element 116 including a filament portion 118 and an aggregate polymeric portion 120, an anchor 122, a stretch resistant member 124, and a distal bead 126. The interconnection of these elements is discussed below.

According to one embodiment, the therapeutic element 140 may be secured to the distal end of the flexible tube 102 without entering the lumen of the flexible tube or only partially entering the lumen. In this embodiment, the therapeutic element and the flexible tube may both fit within another outer tube or guiding catheter for atraumatic delivery. In another embodiment, the therapeutic element may fit within the distal end of the flexible tube so that it may be introduced through the flexible tube without need for another outer guiding catheter.

The capability of the coupling union 130 to be thermally decoupled to deploy the therapeutic element is beneficial in that it allows prompt precise placement of the therapeutic element at the target site. Whereas prior art devices have relied upon pusher wires and other ejection mechanisms that exert an often unpredictable force on the therapeutic element to deploy it, the thermally activated coupling union according to various embodiments of the present invention can be quickly and easily decoupled without uncontrollably propelling the therapeutic element from the delivery tube. This is desirable as uncontrolled therapeutic elements that shoot away from the tube may result in inaccurately placed coils or coils that dislodge other previously placed coils.

Within the flexible tube at least one electrical conductor is provided. For example, there may be a positively charged electrical conductor 104 and a negatively charged electrical conductor 106. The electrical conductors are attached to a thermally responsive element 112 or resistive heating element through attachment points 108, 110. The thermally responsive element 112 may, but need not, have a looped or coiled configuration. A hook 114 may also be provided to secure a filament portion 118 of a polymeric element 116 to the thermally responsive element 112 and through the thermally responsive element to at least one electrical conductor, thereby enabling the thermally responsive element 112 to transfer heat to the polymeric element 116 through the proximal filament 118.

In addition to being engaged with the hook 114, the polymer filament 118 may be disposed between the flexible tube 102 and the therapeutic element 140, extending partially within the interior or inner lumen of both the tube 102 and the therapeutic element 140. According to one embodiment the polymer filament 118 at a proximal end of the therapeutic element 140 may loop through a distal loop of the thermally responsive element 112.

In order to ensure the filament portion 118 of the polymeric element 116 only breaks at a spatially limited, preselected location after heating to the appropriate temperature, the filament may have a reduced thickness or diameter at the desired breakpoint location that is smaller than for the rest of the securing filament. Or, the filament may be insulated except at the desired breakpoint location or exhibit a greater responsiveness to heat absorption at the desired breakpoint location on account of composition or physical differences.

The polymeric element 116 also includes an aggregate polymeric portion 120 secured to an anchor 122. For example, the anchor 122 may be U-shaped and disposed around the aggregate portion 120 of the polymeric element 116. The anchor 122 may be formed of metal or another material resistant to deformation at the temperature that causes deformation of the polymeric element 116. The anchor 122 and at least the aggregate portion 120 of the polymeric element 116 are disposed within the therapeutic element 140. For example, an outer surface of the anchor 122 may be disposed adjacent an inner surface 142 of a loop of an embolic coil 144. The anchor may be secured to the aggregate portion of the polymeric element and the embolic coil loop by adhesives, solder, welding, friction fit, outward bias, and the like.

The polymeric element 116 may be formed of, for example, a polyolefin, such as polyethylene or a polyamide, such as nylon, or a polyester, such as PET, or a fluoropolymer, such as polytetrafluoroethylene (PTFE), and the like.

The anchor 122 is connected to a stretch resistant member 124 at its distal end. For example, the stretch resistant member 124 may loop through a U-shaped anchor 122. The stretch resistant member may be formed as a ribbon, wire, braid, primary wind, or stranded material, and may be formed from fiber, plastic or other polymer such as an ethylene-octene copolymer, polypropylene, or polyethylene, or a metal or metal alloy, such as a nickel-titanium alloy, for example, or a metal which is radiopaque, such as platinum, for example.

The stretch resistant member 124 forms or is attached to a bead 126 formed of the same type of polymeric material as the stretch resistant member at its distal end. A distal outer surface of the bead may be substantially hemispherical 128, curved, or rounded so as to facilitate an atraumatic introduction of the therapeutic element 140, and the bead is secured to the distal end of the embolic coil, such as by melting of the polymeric material forming the bead, for example. The bead 126 holds the therapeutic element 140 in a first compressed configuration 150 in which the therapeutic element is retained to the delivery tube 102. When the connection between the polymeric element 116 and the hook 114 is severed via heating of the filament 118, the therapeutic element 140 is released and transforms from the first compressed configuration 150 to a second deploying configuration 160. The stretch resistant member 124 may, but need not, be integrally formed with the distal bead 126. For example, the distal bead 126 may be formed by melting the polymeric or other material used to form the stretch resistant member 124.

Heating of the polymeric element may sever the connection between the therapeutic element and the heating and delivery system through the filament in any number of ways. For example, according to one embodiment, the filament may be formed of a polymeric material that melts and splits into two or more sections thereby disengaging from the connector that secures it to the heating and delivery system. This connector may be the hook 114.

As another example, according to another embodiment, the filament may be formed of a shape memory polymeric (SMP) material that changes shape upon heating above a certain phase transformation temperature. The phase transformation depends on the specific SMP material used and the SMP material selected or designed for this application may be tailored to have a desired phase transformation temperature. The change in configuration may induce the filament to release itself from the connector that secures it to the heating and delivery system.

Most shape memory polymers can retain two shapes, and the transition between those is induced by temperature. In some recent shape memory polymers, heating to certain transition temperatures allows a fix of up to three different shapes. In addition to temperature change, the shape change of shape memory polymers can also be triggered by an electric or magnetic field, light or solution. Shape memory polymers can also have a wide variety of other properties that can change between first and second different states or conditions, or among three different states or conditions, such as from stable to biodegradable, from soft to hard, from elastic to rigid, and the like depending on the structural units that constitute the shape memory polymers. Shape memory polymers that can be used in the present invention include thermoplastic and thermoset (covalently crosslinked) polymeric materials.

The material used to form the filament portion of the polymeric element is designed in order that it melts, splits, or undergoes a phase transformation at a temperature sufficiently above normal body temperature and febrile temperatures so that it is not prematurely activated. The heat necessary to achieve this higher decoupling temperature can be supplied by an auxiliary electrical heating system or an alternative energy source. For example, there may be electrical conductors 104, 106 and a resistive heating coil 112 disposed within the body of the flexible delivery tube. Alternatively, there may be a laser or optical fiber (not shown) in the tube in thermal communication with the polymeric filament 118.

Preferably, the polymeric element 116 and distal bead 126 are formed of non-toxic, biocompatible materials that may also be biodegradable, bioabsorbable or bioerodible such that when they are melted or undergo a change in configuration as a result of a phase change transformation they do not pose a hazard from being loose in the bloodstream.

According to one of several embodiments, the therapeutic element delivery system as described herein is capable of operating in small (250-500 micrometers) diameter applications, such as may be found in veins and arteries of the human brain, which enables catheter-based devices to reach and treat an aneurysm in the brain.

It will be apparent from the foregoing that while particular forms of the invention have been illustrated and described, various modifications can be made without departing from the spirit and scope of the invention. Accordingly, it is not intended that the invention be limited, except as by the appended claims.

I claim:

1. A therapeutic actuator for securing a therapeutic element having a compressed configuration to a heating and delivery system, comprising:
    a bead on a distal end of the therapeutic element; and
    a coupling union including a polymeric element and an anchor configured to secure said bead to the heating and delivery system to retain the therapeutic element in the compressed configuration, said polymeric element including an aggregate portion, a filament portion connected to said aggregate portion, said aggregate portion being disposed within an internal lumen defined by the therapeutic element, said anchor being disposed outside the aggregate portion of the polymeric element and fixedly attached to the aggregate portion of the polymeric element between an outer surface of the aggregate portion and an inner surface of the therapeutic element.

2. The therapeutic actuator of claim 1, wherein a distal face of the bead has a hemispherical shape.

3. The therapeutic actuator of claim 1, wherein a distal face of the bead has a curved outer surface that facilitates atraumatic introduction of the therapeutic element.

4. The therapeutic actuator of claim 1, wherein the therapeutic element is an embolic coil configured for treatment of an aneurysm.

5. The therapeutic actuator of claim 1, further comprising a flexible tube defining a lumen therein wherein the therapeutic element is configured to be retained to the flexible tube,
    wherein the heating and delivery system comprises an electrical conductor disposed within the lumen of the flexible tube and a resistive heating element also disposed within the lumen of the flexible tube distal to the electrical conductor and electrically connected to the electrical conductor; and
    the filament portion is connected to the resistive heating element and the aggregate portion positioned inside the therapeutic element and distal to the filament portion.

6. The therapeutic actuator of claim 5, further comprising a thermally conductive hook interposed between the filament portion and the resistive heating element, the hook connecting the filament portion of the polymeric element to the resistive heating element.

7. The therapeutic actuator of claim 5, wherein the therapeutic actuator is configured such that the filament portion is disconnectable from the resistive heating element to release the bead and deploy the therapeutic element from a distal end of the flexible tube by melting the polymeric element through energy supplied by the electrical conductor that heats the resistive heating element.

8. The therapeutic actuator of claim 5, wherein the polymeric element is formed of a shape memory material that undergoes a phase transformation at a phase transformation temperature whereby heating the material above the phase transformation temperature enables the material to soften and be reshaped to another configuration in which the filament portion disconnects from the resistive heating element and releases the bead to deploy the therapeutic element from a distal end of the flexible tube.

9. The therapeutic actuator of claim 5, wherein the electrical conductor comprises a positively charged electrical conductor and a negatively charged electrical conductor.

10. The therapeutic actuator of claim 1, wherein the anchor has a horseshoe shape.

11. The therapeutic actuator of claim 1, further comprising a stretch resistant member configured to secure the bead to the anchor.

12. The therapeutic actuator of claim 11, further comprising a thermally conductive hook disposed between the filament portion and the heating and delivery system, the hook connecting the filament portion of the polymeric element to the heating and delivery system.

13. The therapeutic actuator of claim 1, further comprising a thermally conductive hook interposed between the filament portion and the heating and delivery system, the hook connecting the filament portion of the polymeric element to the heating and delivery system.

* * * * *